United States Patent
Hadash

(10) Patent No.: US 10,434,275 B2
(45) Date of Patent: Oct. 8, 2019

(54) BODY CORE TEMPERATURE COOLING DEVICE

(71) Applicant: INHALETECH LLC, Minneapolis, MN (US)

(72) Inventor: Joseph Hadash, Lapid (IL)

(73) Assignee: Inhaletech LLC, Minneapolis, MN (US)

(*) Notice: Subject to any disclaimer, the term of this patent is extended or adjusted under 35 U.S.C. 154(b) by 0 days.

(21) Appl. No.: 15/023,061

(22) PCT Filed: Sep. 17, 2014

(86) PCT No.: PCT/IL2014/050829
§ 371 (c)(1),
(2) Date: Mar. 18, 2016

(87) PCT Pub. No.: WO2015/040614
PCT Pub. Date: Mar. 26, 2015

(65) Prior Publication Data
US 2016/0228669 A1 Aug. 11, 2016

Related U.S. Application Data

(60) Provisional application No. 61/960,404, filed on Sep. 18, 2013.

(51) Int. Cl.
*A61M 16/06* (2006.01)
*A61M 16/00* (2006.01)
(Continued)

(52) U.S. Cl.
CPC ....... *A61M 16/1075* (2013.01); *A61F 7/0085* (2013.01); *A61M 16/0003* (2014.02);
(Continued)

(58) Field of Classification Search
CPC ........ A61M 16/00; A61M 16/06–0694; A61M 16/20–209; A61M 2016/0003–0042;
(Continued)

(56) References Cited

U.S. PATENT DOCUMENTS 2,591,992 A * 4/1952 Aerick .................. A61F 7/007
128/203.27
3,688,770 A 9/1972 O'Neill
(Continued)

FOREIGN PATENT DOCUMENTS

CN 201248938 Y 6/2009
WO WO 03/047603 A2 6/2003
(Continued)

OTHER PUBLICATIONS

Patent Cooperation Treaty, International Search Report, International Patent Application No. PCT/IL2014/050829, dated Dec. 29, 2014, 7 Pages.
(Continued)

*Primary Examiner* — Tan-Uyen T Ho
*Assistant Examiner* — Ned T Heffner
(74) *Attorney, Agent, or Firm* — Fenwick & West LLP

(57) ABSTRACT

A portable body-cooling device, comprises: a mask suitable to be positioned on the face of the patient and to cover its mouth and nose; a connector, suitable to connect said mask to a breathable gas container; and a gas container, containing a breathable gas in compressed state, which, when expanded, undergoes cooling. Also described is a method for reducing the body temperature of the patient in need thereof.

15 Claims, 5 Drawing Sheets

(51) Int. Cl.
*A61M 16/10* (2006.01)
*A61M 19/00* (2006.01)
*A61F 7/00* (2006.01)
*A61M 16/08* (2006.01)

(52) U.S. Cl.
CPC ........ *A61M 16/06* (2013.01); *A61M 16/0605* (2014.02); *A61M 16/0816* (2013.01); *A61M 19/00* (2013.01); *A61F 2007/0064* (2013.01); *A61F 2007/0096* (2013.01); *A61M 16/0683* (2013.01); *A61M 2016/0027* (2013.01); *A61M 2016/0036* (2013.01); *A61M 2205/3561* (2013.01); *A61M 2205/3584* (2013.01); *A61M 2205/3592* (2013.01); *A61M 2205/3606* (2013.01); *A61M 2205/502* (2013.01); *A61M 2230/06* (2013.01); *A61M 2230/40* (2013.01); *A61M 2230/50* (2013.01)

(58) Field of Classification Search
CPC .. A61M 39/00; A61M 39/10; F16L 11/00–26; A61F 7/00; A62B 7/00; A62B 7/04; A62B 7/14; A62B 18/00; A62B 18/10; A61B 9/00; A61B 9/02–027; A61B 18/02–0218; A61B 2018/0212–0293; B63C 11/12; B63C 11/18
See application file for complete search history.

(56) References Cited

U.S. PATENT DOCUMENTS

| | | | |
|---|---|---|---|
| 5,027,807 A * | 7/1991 | Wise | A62B 17/005 128/201.28 |
| 5,435,299 A * | 7/1995 | Langman | A62B 9/003 128/201.13 |
| 7,958,893 B2 | 6/2011 | Lithgow et al. | |
| 8,100,123 B2 * | 1/2012 | Belson | A61F 7/0085 128/200.14 |
| 2004/0064171 A1* | 4/2004 | Briscoe | A61F 7/02 607/104 |
| 2005/0103353 A1* | 5/2005 | Grahn | A61F 7/02 128/898 |
| 2009/0107491 A1 | 4/2009 | Belson | |
| 2010/0042013 A1* | 2/2010 | Cuesta Frau | A61B 5/0008 600/549 |
| 2011/0295163 A1* | 12/2011 | Vijayanagar | A61F 7/02 601/18 |

FOREIGN PATENT DOCUMENTS

| WO | WO 2005/070035 A2 | 8/2005 |
|---|---|---|
| WO | WO 2010/065616 A1 | 6/2010 |

OTHER PUBLICATIONS

Patent Cooperation Treaty, Written Opinion of the International Searching Authority, International Patent Application No. PCT/IL2014/050829, dated Dec. 29, 2014, 6 Pages.

Patent Cooperation Treaty, International Preliminary Report on Patentability, International Patent Application No. PCT/IL2014/050829, dated Jun. 14, 2015, 11 Pages.

European Extended Search Report, European Application No. 14845345.9, dated Feb. 8, 2017, 7 pages.

* cited by examiner

BODY CORE TEMPERATURE COOLING DEVICE

FIELD OF THE INVENTION

The present invention relates to a device and a method for decreasing body temperature.

BACKGROUND OF THE INVENTION

Body core temperature (hereinafter also referred to simply as "body temperature") is an important parameter that influences physical systems of the body, and can determine the way in which the body will respond under different conditions.

There is a high correlation between body temperature and metabolic rate. The metabolism is an energy-production process, and its rate is affected, among other factors, by the temperature of the environment. To keep a normal body temperature in a cold environment, the metabolic rate will increase, in order to produce energy that releases heat and warms up the body.

A higher metabolic rate automatically inflicts a faster activity of different physical systems of the body, and increases body temperature. The correlation between body temperature and metabolic rate works in both directions, so that if the body temperature changes, it also causes the metabolic rate to change accordingly.

In some cases, an increase of body temperature can be undesirable, since it causes a higher metabolic rate, which can bring to a progression of destructive processes in the body as well. According to medical researches, usually, the greater damage to the body is formed over the first few minutes after an injury. It is especially crucial when experiencing a stroke or a cardiologic episode, since they are very often followed by long-term physical complications.

After cardiac arrest with no blood flow for more than five minutes, the generation of free radicals, together with other mediators, during reperfusion creates chemical cascades that result in cerebral injury. Until recently, there was no therapy with documented efficacy in preventing brain damage after cardiac arrest.

Strokes happen when blood flow to the brain stops. Within minutes, brain cells begin to die. There are two kinds of stroke. The more common kind, called ischemic stroke, is caused by a blood clot that blocks or plugs a blood vessel in the brain. The other kind, called hemorrhagic stroke, is caused by a blood vessel that breaks and bleeds into the brain. "Mini-strokes" or transient ischemic attacks occur when the blood supply to the brain is briefly interrupted. In traumatic head injury not only can result in immediate seizures, it often causes chronic seizures which are frequently resistant both to medication and surgical intervention.

Another example is epilepsy, which is a brain disorder that causes people to have recurring seizures. The seizures happen when clusters of nerve cells, or neurons, in the brain send out the wrong signals. People may have strange sensations and emotions or behave strangely. They may have violent muscle spasms or lose consciousness. Post-traumatic epilepsy is prevalent, often difficult to manage, and currently cannot be prevented.

In hospitals, doctors use a cooling-cell to decrease the body temperature of patients who suffer from injuries that can cause long-term damages, and induce a mild therapeutic hypothermia. Although the cooling-cells in hospital can minimize the extent of injuries, it is crucial to cool the body as soon as possible, and sometimes it takes too long to get to a hospital, and in any event, the patient is not treated immediately.

Another disadvantage of cooling-cells is the fact that they do not prevent the involuntary reaction of the human body to a decrease in body temperature, which is a tremor of the muscles that obtains the opposite of the desired effect, e.g., a raise in body temperature.

Therefore, it is an object of the present invention to provide a device suitable to cause an immediate cooling of the body, which can be operated outdoors, and can be taken to where the patient is located.

It is another object of the invention to provide a portable device that can be operated and stored essentially everywhere, so as to be available immediately when needed.

It is a further object of the invention to provide a method for cooling the human body, which is simple to operate by a non-skilled operator, and which can be performed whenever needed, without prior extensive preparations.

It is yet another object of the present invention to provide a device and method that overcome the drawbacks of the prior art, such as the inability to prevent involuntary tremor of the muscles.

Other objects and advantages of the invention will become apparent as the description proceeds.

SUMMARY OF THE INVENTION

The device relates to a portable body-cooling device, comprising: a mask suitable to be positioned on the face of the patient and to cover its mouth and nose; a connector, suitable to connect said mask to a breathable gas container; and a gas container, containing a breathable gas in compressed state, which, when expanded, undergoes cooling.

The connector can be provided with an orifice suitable to allow the expansion of a compressed gas, thus causing the cooling of said compressed gas. The connector can also be provided with a Vortex tube that separates streams of gases into hot and cold streams. A gas expansion chamber can be provided within the connector, or it can be coupled to the gas container or to the mask.

The mask can be provided with a portion located around its contacts area with the face of the patient, which can be heated to avoid involuntary tremor of the muscles. The portion can be, for example, an inflatable portion suitable to host gases, such as the patient's exhaled breath, or fluids. Another exemplary portion is a portion that can be heated by electrical means. Alternatively, the mask can be provided with a material capable of absorbing and releasing heat, such as a textile material.

The device can be further provided with one or more sensors of body functions, such as pressure or flow sensors that will indicate an inhalation or an exhalation of the patient, temperature sensors, and hart rate sensors.

The device can also comprise a display suitable to display information on the operation of the device and/or the patient's body parameters, and can comprise wired or wireless connection elements suitable to operably connect a smartphone, a tablet or the like device, such as to read data relating to the functioning of the device and/or the condition of the patient, and, optionally, to transmit said information or part thereof to a remote location.

The invention also relates to a system, comprising the device of the invention and a processor suitable to activate one or more valves as a result of a sensed parameter relating to patient's body activity. One or more of the processors can be provided in an external device, which can be portable, like a smartphone.

The invention also relates to a method for reducing the body temperature of a patient in need thereof, comprising: providing a mask suitable to be positioned on the face of the patient and to cover its mouth and nose; providing a connector, suitable to connect said mask to a breathable gas container; providing a gas container, containing a breathable gas in compressed state, which, when expanded, undergoes cooling; and applying said mask to the face of a patient, connecting the gas container to said mask via said connector, and causing gas to flow through an expansion device such as to be cooled before flowing into the inhalation inlet of said mask.

BRIEF DESCRIPTION OF THE DRAWINGS

The invention will be further illustrated with reference to the appended drawings, wherein.

DETAILED DESCRIPTION OF THE INVENTION

Body warmth has a great influence on the metabolic rate of the body, which controls different processes in the body. As explained in the background of the invention, and as indicated according to medical researches, in some injuries, the aim of caregivers is to decrease the body temperature of the patient in order to minimize the extent of long-term complications.

Nowadays, most cooling devices used for such purposes, cool the body by cooling the environment around the body by convection, or by cooling the surfaces of the body by conduction. Cooling processes of those kinds require adsorption of heat from a relatively large volume or surface, which takes a relatively long period of time. In addition, the cooling devices according to the prior art are not portable and are usually only available in hospitals.

The present invention relates to a device and method for cooling the human body by utilizing the cardio-vascular system as a temperature-conduction system. The oxygen that we breathe binds to the red blood cells and travels through the blood stream to reach all the organs. If the air we breathe is at a lower temperature than the temperature of the body, when in contact, the air will adsorb the heat of the body, and as a result, the different organs will lose heat and their temperature will decrease.

Figure 1:
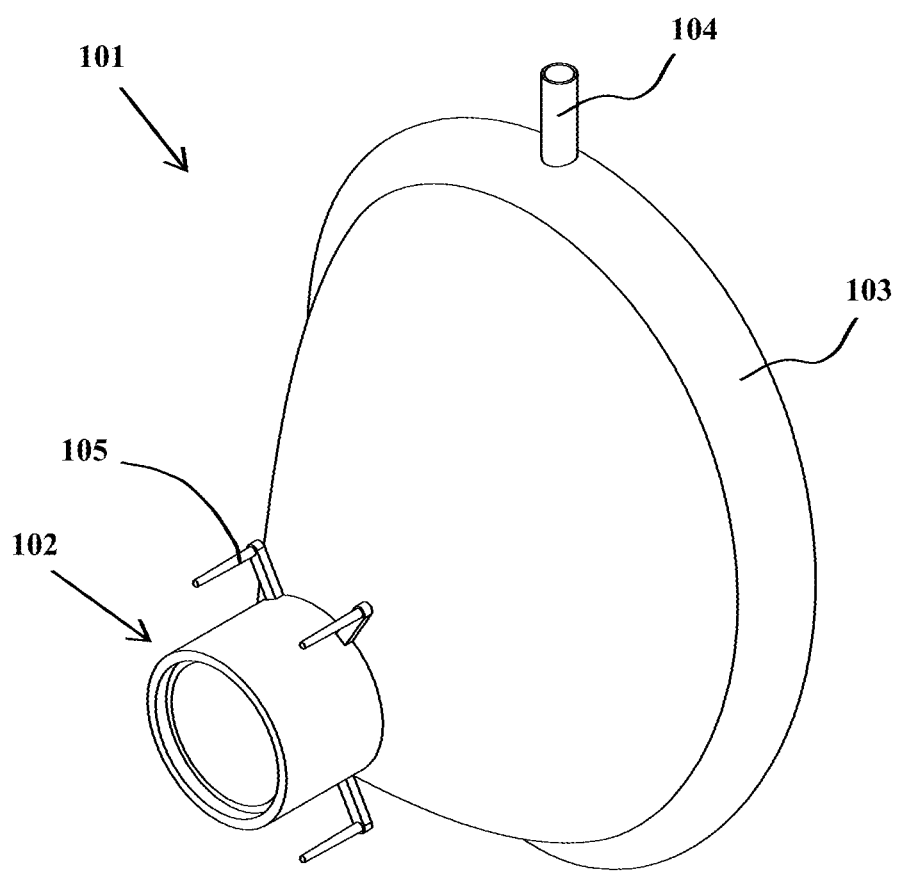
FIG. 1 is a perspective view of the device, according to one embodiment of the invention, showing a mask.

FIG. 1 is a perspective view of a device, according to one embodiment of the invention, showing mask 101. Mask 101 is suitable to be placed around the breathing openings (the nose and mouth), so it is designed to surround them. Mask 101 comprises gas opening 102, through which breathable gas is inserted. An example of breathable gas is, for example, oxygen-enriched air.

Mask 101 also comprises surrounding inflatable portion 103 that is necessary for separating the breathing openings from the environment. Inflatable portion 103 provides a direct flow of air (or other breathable gases) from gas opening 102 into the nose and mouth of the person wearing mask 101, without letting the air escape from the inner volume of mask 101, as will be further illustrated in FIG. 2B.

Figure 2:
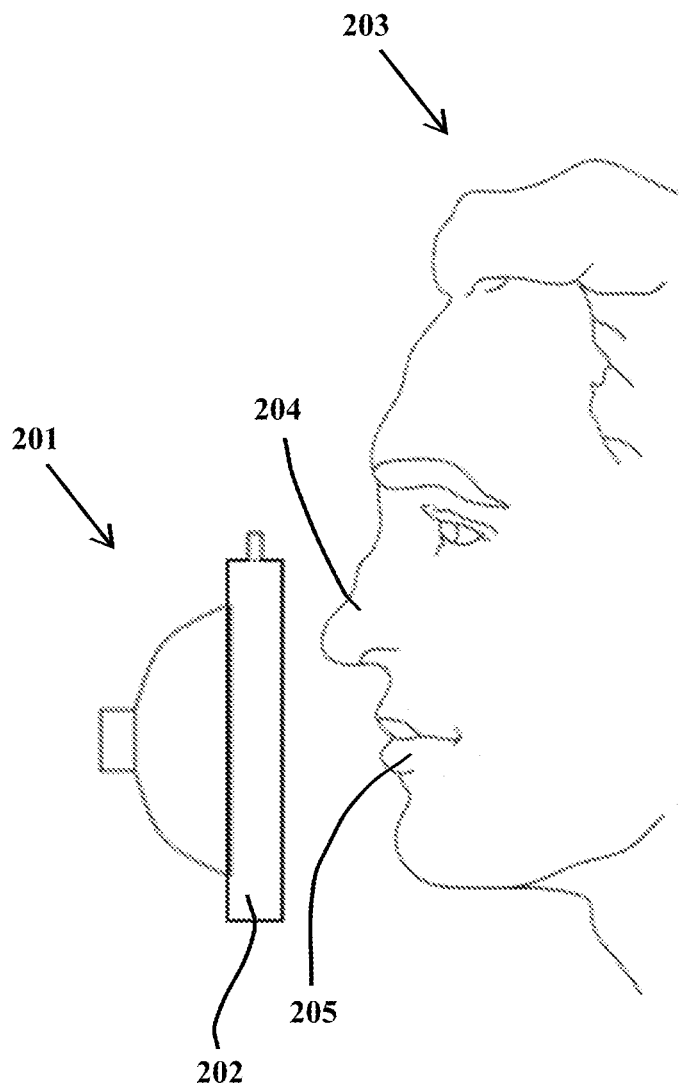
FIG. 2 is a side view of a second device, according to another embodiment of the invention, and a patient, illustrating the positioning of the mask on the patient.

FIG. 2 is a side view of an alternative mask 201 about to be placed on a patient's face and illustrating the positioning thereof around the patient's breathing openings, according to another embodiment of the invention, with an inflatable portion indicated by numeral 202. Inflatable portion 202 is in contact with the face of patient 203, surrounding his nose 204 and mouth 205.

Using inflatable portions around air-supplying masks is very common because it prevents air from escaping the inner volume of a mask to the environment, and therefore ensures that essentially all of the air that is supplied through the mask will be inhaled by the patient.

According to medical research, it has been proven that the area of the body that senses cold temperatures and sets the natural and automatic tremor reaction in motion is the area that surrounds the breathing opening. As hereinbefore explained, the purpose of the tremor reaction is to move the muscles and release heat that will warm up the body. When trying to cool the body, it is best to avoid the tremor reaction, and the present invention provides a solution for that problem, as will be further described hereinafter.

The inflatable portion of the mask, according to the present invention, is also suitable to host warm materials and function as a warming component that warms up surfaces with which it is in contact, like the skin that surrounds the breathing openings that are in contact with the inflatable portion. FIG. 1 shows inflatable portion inlet 104, through which materials, such as a warm gas, can flow into inflatable portion 103. The materials can be of any type of materials that will warm up the area that is in contact with inflatable portion 103, for example, warm air exhaled by the patient.

In the embodiment of FIG. 1 there is no continuous flow of gas into inflatable portion 103, since no outlet is provided. Hence, portion 103 is inflated and then flow is stopped. However, in another embodiment the device can further comprise an outlet. For instance, in the embodiment of FIG. 1 the outlet can be located anywhere on the circumference of inflatable portion 103, similarly to inflatable portion inlet 104, which allows the output of warming substances from inflatable portion 103. If, for example, the material that flows into inflatable portion 103 through inflatable portion inlet 104 is warm air, it can be pushed out through said additional outlet, which provides a continuous flow of warm air through the inner space of inflatable portion 103.

An alternative component that can replace inflatable portion 103, according to another embodiment of the invention, is a portion of a material that can keep a warm environment, such as textile fabric that is often used in ski face masks, because it retains outbreath heat and thus warms up the surrounding of the breathing opening.

FIG. 1 also shows hooks 105 of a conventional type, which may or may not be present. Such hooks are usually used for positioning and securing a mask onto the face of a patient and around his breathing openings. The positioning of mask 101 by hooks 105 can be operated by stretching a flexible string and positioning it between hooks 105 and the back of the ears of the patient. Securing the mask around the breathing openings of a patient provides the freedom for a care-giver to operate and monitor the process with both hands, without the need to assure a proper positioning of the mask on the patient's face.

The device of the invention is small enough to be stored inside a medical bag, a glove compartment, etc., and can be taken to the field for immediate medical attention, if needed. Therefore, the present invention provides the possibility to use a body-cooling device outside of a hospital, which is a significant advantage, compared to the prior art, especially when taking under consideration the need for an immediate body-cooling treatment when facing injuries that can cause long-term damages, which can be avoided or at least minimized if the body temperature of the patient is decreased soon enough.

Figure 3:
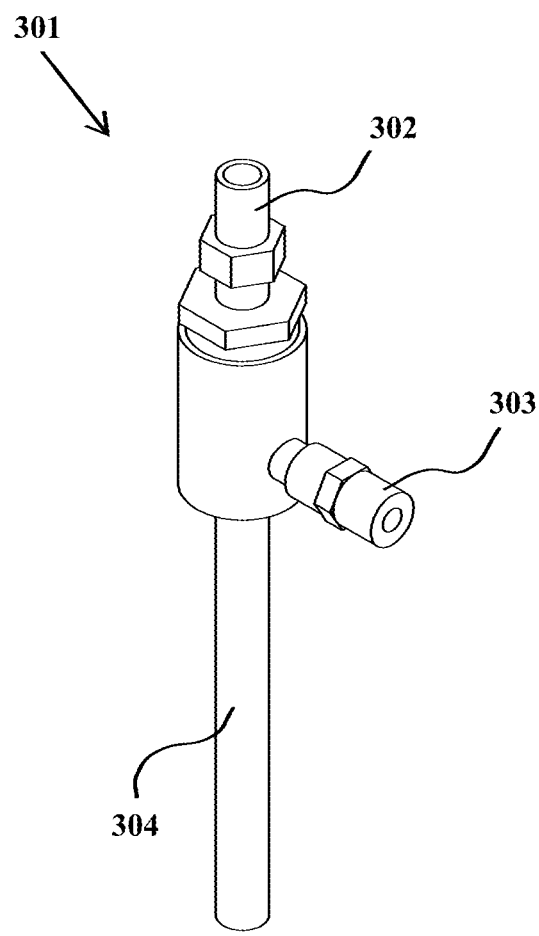
FIG. 3 is a perspective view of a connector that can be coupled to the gas opening of a mask.

Gas opening 102 of the mask of FIG. 1 is suitable to be coupled to a container that contains a gas material that can be inhaled. FIG. 3 is a perspective view of connector 301, which is a type of vortex tube (see, e.g., http://en.wikipedia.org/wiki/Vortex_tube) that can be coupled to gas opening 102 by entry opening 302. Connector 301 comprises gas inlet tube 303 that can be connected to a gas container, and gas outlet tube 304. When a gas container is connected to gas inlet tube 303, it allows the gas to flow into connector 301 toward entry opening 302 and gas outlet tube 304. Of course, many different connectors can be employed, and this is just one illustrative example.

Figure 4:
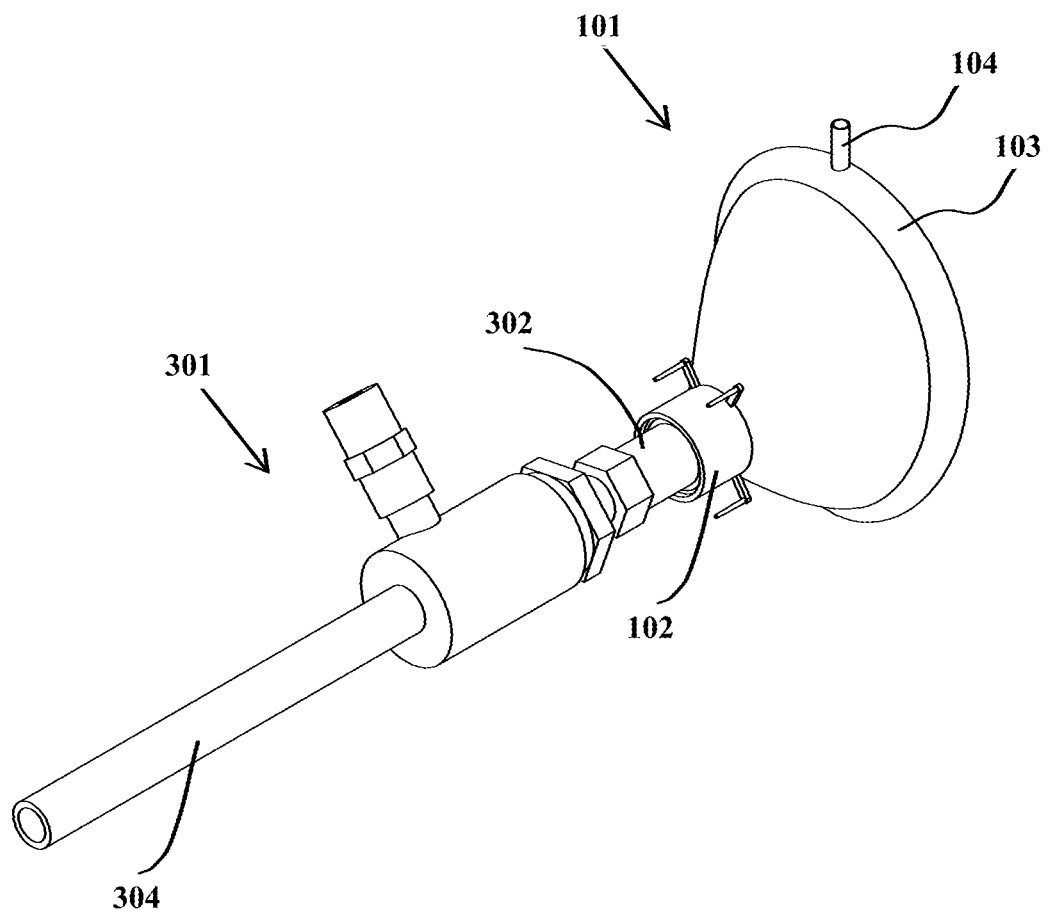
FIG. 4 is a perspective view of the mask of FIG. 1 and the connector of FIG. 3, when the gas opening of the mask and the entry opening of the connector are connected.

FIG. 4 is a perspective view of mask 101 of FIG. 1 and connector 301 of FIG. 3, when gas opening 102 and entry opening 302 are connected. When gas flows through entry opening 302 into the inner volume of mask 101 it spreads and the pressure of the gas naturally drops, which causes the temperature of the gas to decrease. As will be apparent to the skilled person, allowing the gas to expand through an orifice, located within the connector, will cause the compressed gas to cool. Connector 301 is also provided with an inner structure, such as the aforementioned Vortex tube, which separates the gas stream into hot and cold streams, the cold stream being directed toward the mask and the hot stream being exhausted and, if desired, partly used to heat the inflatable portion.

The term "inflatable portion", as used herein, is not limited to materials that can be inflated and is used, for the sake of brevity, also to indicate a chamber through which gas or other material can flow, even if the flow does not cause inflation of the chamber.

In one embodiment of the invention, when no Vortex tube is used and heating of the mouth area is obtained by retaining the heat of the exhaled breath, a suitable textile material is provided in the area surrounding the lips and nose of the patient, or in part of it.

In order to cause the gas to flow into the inner volume of mask 101 only when the patient is inhaling, the device can be further provided with a sensor that detects the timing of inhalation and signals a processor to allow gas to flow from the gas container and into the inner volume of mask 101, e.g., by actuating a valve that regulates the flow of the gas, and the processor can be a processor that is located within the device, or it can be an external processor that communicates with the device, such as a smartphone. Employing an external processor allows to simplify the device and to reduce its size. Moreover, it allows to upgrade the performance of the device as new and improved smartphones become available, with stronger processors.

Suitable software can be provided on the external processor, to operate the device, and in the case of a smartphone an application can be used, which can be readily available from the relevant app store to a smartphone user or to a user of another suitable device, such as a tablet.

Gas outlet tube 304 can be further attached to another tube that can be connected to inflatable portion inlet 104. The gas that flows through gas outlet tube 304 does not expand and therefore keeps a temperature that is higher than the temperature of the gas that flows into the inner volume of mask 101, so it can be used to warm the surface that comes in contact with inflatable portion 103.

Connector 301 can be replaced with any other type of connector that provides the flow of breathable gas through gas opening 102, and it does not necessarily need to be provided with an outlet tube such as gas outlet tube 304. The connector can comprise a valve that will help determined the flow rate and amount of gas released into gas opening 102.

When a patient that wears the mask of the device exhales, the exhaled air needs to escape the inner volume of the mask. The release of exhaled air can be obtained by one-way-valve(s) that is connected to the mask (not shown). An example of such one-way-valve is a valve that opens when pressure increases, for example, as a result of exhaling air into the inner volume of the mask.

The breathable gas can comprise cooling materials, such as mint that is known to be harmless and has a cooling effect on the body. The device can further comprise an adapter that allows the connection of two containers simultaneously, as well as additional sensors, such as a thermometer and a heart-rate measuring component.

Figure 5:
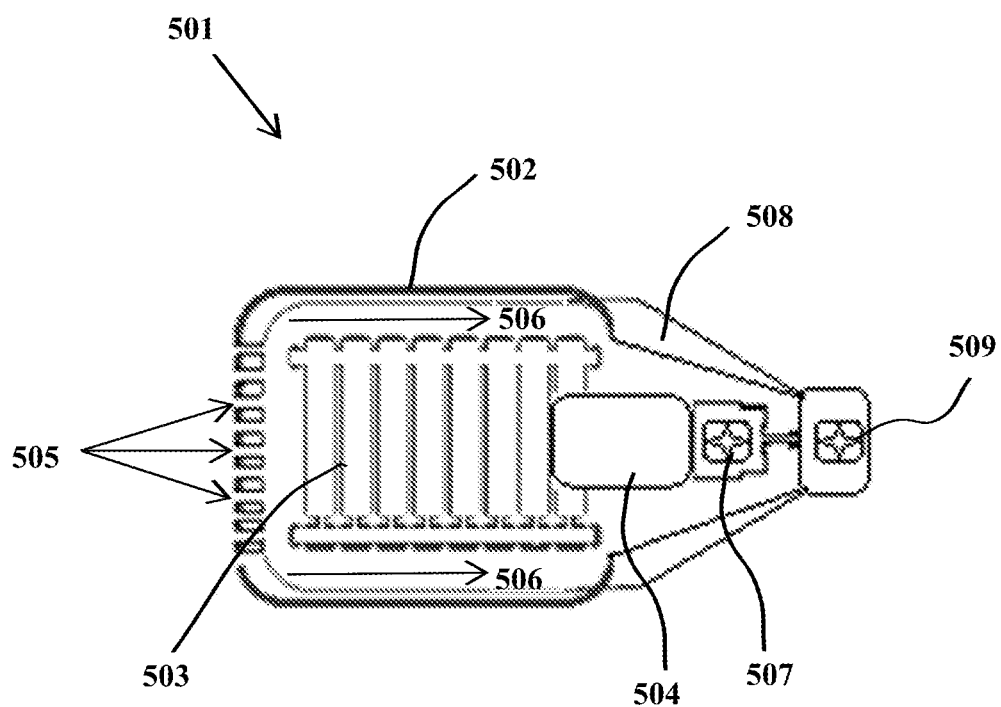
FIG. 5 is a side view of a container, according to yet another embodiment of the invention.

FIG. 5 schematically illustrates a cooling reservoir 501 according to another embodiment of the invention, consisting of the housing 502 that contains a heat exchanger 503, connected to a compressed gas bottle 504.

Alternatively, a low-temperature, liquefied material, such as liquid nitrogen, can be used, instead of a compressed gas. When the patient inhales air flows through openings 505 and around heat exchanger 503, as indicated by arrows 506, flowing on the surface of heat exchanger 503, and thereby being cooled. Bottle 504 is fitted with a valve 507 (the tubing connecting them not being shown, for the sake of simplicity), which can be manually or electronically activated by the user. When valve 507 is actuated gas expands and flows into heat exchanger 503. A suitable connector can be provided, either attached to reservoir 501 or to mask 101, which is not shown for the sake of brevity.

An optional cooling material reservoir 508, containing, for instance, a fragrance such as mint, which is known to provide a cooling effect to the body, can be also coupled to reservoir 501. Further optionally, it may be provided with a valve 509, which can be used to regulate the release of said material into the stream of in breath that has been cooled by heat exchanger 503.

As said, in order to monitor the body temperature throughout the process, the device can be further provided with a temperature-measuring component and an indicator that will remind the care-giver to measure the body temperature of a patient. Measuring body temperature throughout the process is important in order to determine the necessary flow rate and duration of the process, since an overcooling of the body can also cause damages, such as hypothermia.

The temperature-measuring component can be a conventional thermometer that measures the temperature of the surface with which it comes in contact, like thermometers that can be attached to the forehead of a patient, or it can be a component that measures the exhaled air of the patient, e.g., a thermocouple. The temperature of the exhaled air can be set as a reference point and can be used to calculate the body temperature of the patient, when taking under consideration physical indicators, such as the weight and age of the patient.

The device can also be provided with a screen that shows data, such as the current body temperature, the duration of the process, hart rate, etc., or it can be connected to a smart phone instead, since smartphone devices are nowadays provided with powerful CPUs and with a variety of sensors that can be used for such purposes. The gathered data can be important while providing the treatment, can be sent on to the medical team that will treat the patient, and can also be used further on at a hospital.

All the above description has been provided for the purpose of illustration and is not meant to limit the invention in any way.

The invention claimed is:

1. A portable device for cooling a body core simply by expanded breathable gas while warming up skin surrounding a mouth of a patient after a stroke, a cardiologic episode, or a traumatic event, comprising:
    a) a mask suitable to be positioned on the face of a patient and to cover its mouth and nose, comprising a gas opening through which said breathable gas is inserted;
    b) a connector, suitable to connect said mask via an entry opening to a breathable gas container;
    c) a gas expansion chamber, coupled to said connector;
    d) a gas container, containing a breathable gas selected from air and oxygen-enriched air in compressed state, which, when expanded in said chamber, undergoes cooling and cools said body core simply by said expanded gas;
    e) a warming component to contact the skin that surrounds the breathing openings of said patient including said mouth, warming up said skin surrounding the mouth simply by air exhaled by said patient;
    f) a heart rate sensor and one or more sensors of other body functions including patent's inhalation or exhalation; and
    g) a processor suitable to activate one or more valves regulating said gas opening and/or said entry opening in response to sensed parameters from said heart rate sensor and said one or more sensors of other body functions;
    wherein said breathable gas without being cooled otherwise than by expansion in said chamber absorbs the heat of the body when breathed in thereby reducing the body core temperature, and wherein said warming component warms up said skin only by the patient's own exhaled breath as a heating medium thereby preventing involuntary tremor reaction of the body, so minimizing the extent of cerebral injuries caused by said stroke, said cardiologic episode, or said traumatic event, the way of said cooling the body core and warming said skin rendering said device compact and portable.

2. A device according to claim 1, wherein the connector is provided with an orifice through which said gas expands.

3. A device according to claim 1, wherein said warming component is inflatable, and the patient's exhaled breath is a heating medium.

4. A device according to claim 1, wherein said gas expansion chamber is provided within said connector.

5. A device according to claim 1, wherein said gas expansion chamber is provided in, or coupled to, said gas container.

6. A device according to claim 1, wherein said gas expansion chamber is provided in, or coupled to, said mask.

7. A device according to claim 1, provided with one or more temperature sensors.

8. A device according to claim 1, further comprising a display suitable to display information on the operation of the device and/or the patient's body parameters.

9. A device according to claim 1, further comprising wired or wireless connecting elements suitable to operably connecting a smartphone or a tablet, such as to read data relating to the functioning of the device and/or the condition of the patient, and to transmit said information or part thereof to a remote location.

10. A device according to claim 1, comprising one or more sensors suitable to detect inhalation and/or exhalation by the patient.

11. A device according to claim 1, wherein the connector comprises a Vortex tube.

12. A device according to claim 1, further provided in the mask with a material capable of absorbing and releasing heat.

13. A device according to claim 12, wherein the material is a textile material.

14. A system according to claim 1, wherein one or more of a processor and a sensor are provided in an external device.

15. A system according to claim 14, wherein the external device is a smartphone or a portable device.

* * * * *